US010952764B2

(12) United States Patent
Shiber

(10) Patent No.: US 10,952,764 B2
(45) Date of Patent: Mar. 23, 2021

(54) ROTARY CATHETER DRIVE UNIT CONTAINING SEAL-SETS

(71) Applicant: Samuel Shiber, Santa Barbara, CA (US)

(72) Inventor: Samuel Shiber, Santa Barbara, CA (US)

( * ) Notice: Subject to any disclaimer, the term of this patent is extended or adjusted under 35 U.S.C. 154(b) by 0 days.

(21) Appl. No.: 16/531,099

(22) Filed: Aug. 4, 2019

(65) Prior Publication Data

US 2020/0069328 A1    Mar. 5, 2020

Related U.S. Application Data

(63) Continuation-in-part of application No. 15/598,958, filed on May 18, 2017, now Pat. No. 10,413,319, which is a continuation of application No. 14/568,014, filed on Dec. 11, 2014, now abandoned, which is a continuation-in-part of application No.
(Continued)

(51) Int. Cl.
| | | |
|---|---|---|
| *A61B 17/22* | (2006.01) | |
| *A61B 17/3207* | (2006.01) | |
| *B23B 35/00* | (2006.01) | |
| *A61B 17/32* | (2006.01) | |
| *A61B 17/00* | (2006.01) | |
| *B23B 47/28* | (2006.01) | |

(52) U.S. Cl.
CPC ...... *A61B 17/320758* (2013.01); *A61B 17/22* (2013.01); *B23B 35/00* (2013.01); *A61B 2017/00336* (2013.01); *A61B 2017/00734* (2013.01); *A61B 2017/22038* (2013.01); *A61B 2017/22048* (2013.01); *A61B 2017/320044* (2013.01); *A61B 2017/320766* (2013.01); *B23B 47/28* (2013.01); *Y10T 408/03* (2015.01)

(58) Field of Classification Search
CPC .................. A61B 17/320758; A61B 17/22
USPC .................... 310/90; 606/159, 171
See application file for complete search history.

(56) References Cited

U.S. PATENT DOCUMENTS

| 3,584,101 A | 6/1971 | Martz |
|---|---|---|
| 4,091,880 A | 5/1978 | Troutner |

(Continued)

FOREIGN PATENT DOCUMENTS

| GB | 2426456 | 11/2006 |
|---|---|---|
| WO | WO98/38928 | 9/1998 |
| WO | WO99/25412 | 5/1999 |

OTHER PUBLICATIONS

International Search Report, dated Jun. 27, 2011, PCT/US11/031197.

(Continued)

*Primary Examiner* — Terrance L Kenerly

(57) ABSTRACT

A motor drive for a rotary medical device having at least one seal-set which comprises a bore defining bearing, a motor having an output shaft, a flexible shaft, having a diameter smaller than the bearing's bore, being power transmittingly and concentrically connected to the output shaft, a seal, defining a bore that is smaller than the flexible shaft's diameter, being mounted adjacent to the bearing with its bore concentric relative with the bearing's bore, wherein the flexible shaft passing through the bearing's bore which sufficiently deflects it to align it with the second bore to interferencingly fit through it and hydraulically seal it.

6 Claims, 11 Drawing Sheets

Related U.S. Application Data

13/695,232, filed as application No. PCT/US2011/031197 on Apr. 5, 2011, now abandoned, said application No. 14/568,014 is a continuation-in-part of application No. 14/238,983, filed as application No. PCT/US2012/050759 on Aug. 14, 2012, now Pat. No. 9,700,347.

(60) Provisional application No. 61/343,796, filed on May 4, 2010, provisional application No. 61/461,263, filed on Jan. 14, 2011, provisional application No. 61/575,289, filed on Aug. 17, 2011, provisional application No. 61/686,864, filed on Apr. 13, 2012, provisional application No. 61/998,138, filed on Jun. 18, 2014.

(56) References Cited

U.S. PATENT DOCUMENTS

| | | | |
|---|---|---|---|
| 4,732,154 A | 3/1988 | Shiber | |
| 4,819,634 A | 4/1989 | Shiber | |
| 4,842,579 A | 6/1989 | Shiber | |
| 4,883,458 A | 11/1989 | Shiber | |
| 4,886,490 A | 12/1989 | Shiber | |
| 4,894,051 A | 1/1990 | Shiber | |
| 5,002,553 A | 3/1991 | Shiber | |
| 4,990,134 A | 4/1991 | Auth | |
| 5,007,896 A | 4/1991 | Shiber | |
| 5,030,213 A | 7/1991 | Rumberger | |
| 5,042,984 A | 8/1991 | Kensey | |
| 5,116,350 A | 5/1992 | Stevens | |
| 5,306,244 A | 4/1994 | Shiber | |
| 5,334,211 A | 8/1994 | Shiber | |
| 5,653,696 A | 8/1997 | Shiber | |
| 5,681,336 A | 10/1997 | Clement | |
| 5,806,404 A | 9/1998 | Sher | |
| 6,129,734 A | 10/2000 | Shturman | |
| 6,143,009 A | 11/2000 | Shiber | |
| 6,258,052 B1 | 7/2001 | Milo | |
| 6,416,523 B1 | 7/2002 | Lafontaine | |
| 6,440,148 B1 | 8/2002 | Shiber | |
| 6,482,215 B1* | 11/2002 | Shiber | A61B 17/320758 606/159 |
| 6,572,630 B1 | 6/2003 | McGuckin | |
| 6,758,851 B2 | 7/2004 | Shiber | |
| 6,826,833 B1 | 12/2004 | Maier | |
| 7,316,697 B2 | 1/2008 | Shiber | |
| 8,137,369 B2 | 3/2012 | Shturman | |
| 8,236,016 B2 | 8/2012 | To | |
| 8,795,306 B2 | 8/2014 | Smith | |
| 2002/0007190 A1 | 1/2002 | Wulfman | |
| 2002/0029056 A1 | 3/2002 | Hall | |
| 2002/0151918 A1 | 10/2002 | Lafontaine | |
| 2002/0165567 A1* | 11/2002 | Shiber | A61B 17/320758 606/159 |
| 2002/0188276 A1 | 12/2002 | Evans | |
| 2003/0028206 A1 | 2/2003 | Shiber | |
| 2004/0006358 A1 | 1/2004 | Wulfman | |
| 2004/0147947 A1* | 7/2004 | Donofrio | H01H 9/04 606/169 |
| 2005/0119615 A1 | 6/2005 | Noriega | |
| 2008/0004646 A1 | 1/2008 | To | |
| 2008/0306498 A1 | 12/2008 | Thatcher | |
| 2009/0005755 A1 | 1/2009 | Keith | |
| 2009/0069829 A1 | 3/2009 | Shturman | |
| 2009/0149877 A1 | 6/2009 | Hanson | |
| 2010/0121361 A1 | 5/2010 | Plowe | |
| 2011/0152907 A1 | 6/2011 | Escudero | |
| 2012/0172905 A1 | 7/2012 | Lee Shee | |
| 2013/0103046 A1 | 4/2013 | Shiber | |
| 2014/0200599 A1 | 7/2014 | Shiber | |
| 2015/0094733 A1 | 2/2015 | Shiber | |
| 2015/0164541 A1 | 6/2015 | Shiber | |

OTHER PUBLICATIONS

Supplemental European Search Report, dated Jun. 24, 2014, EP11777774.
International Search Report, dated Oct. 23, 2012, PCT/US12/50759.

* cited by examiner

ROTARY CATHETER DRIVE UNIT CONTAINING SEAL-SETS

CROSS REFERENCE TO RELATED APPLICATIONS

The application is a continuation and priority is claimed to commonly assigned, U.S. Patent Application: Ser. No. 15/598,958 by Shiber, entitled "ROTARY CATHETER DRIVE UNIT CONTAINING SEAL-SETS", filed May 18, 2017, which claims priority to U.S. patent application Ser. No. 14/568,014 by Shiber, entitled "ROTARY CATHETER DRIVE UNIT CONTAINING SEAL-SETS", filed Dec. 11, 2014, which claims priority to: 1) U.S. patent application Ser. No. 13/695,232 by Shiber, entitled "ROTARY CATHETER FOR REMOVING OBSTRUCTIONS FROM BODILY VESSELS", filed on Jan. 8, 2013, which claims priority from Pat. Appl. PCT/US2011/031197 filed on Apr. 5, 2011 by Shiber, and entitled "ROTARY CATHETER FOR REMOVING OBSTRUCTIONS FROM BODILY VESSELS", which further claims priority from U.S. Provisional Pat. Appl. Ser. No. 61/343,796, filed on May 4, 2010 by Shiber and entitled "THROMBECTOMY AND ATHERECTOMY CATHETER" and U.S. Provisional Pat. Appl. 61/461,263 filed on Jan. 14, 2011 by Shiber and entitled "CATHETER FOR THROMBECTOMY AND ATHERECTOMY"; and 2) U.S. patent application Ser. No. 14/238,983, now issued as U.S. Pat. No. 9,700,347, filed on Feb. 14, 2014, by Shiber, entitled "ADAPTIVE ROTARY CATHETER FOR OPENING OBSTRUCTED BLOOD VESSELS", which claims priority from Pat. Appl. PCT/US2012/050059 filed on Aug. 14, 2012 by Shiber, and entitled "ADAPTIVE ROTARY CATHETER FOR REMOVING OBSTRUCTIONS FROM BODILY VESSELS", which further claims priority from U.S. Provisional Pat. Appl. Ser. No. 61/575,289, filed on Aug. 17, 2011 by Shiber and entitled "ROTARY CATHETER FOR BREAKING DOWN AND ASPIRATING OBSTRUCTIONS FROM BODILY VESSELS" and U.S. Provisional Pat. Appl. 61/686,864 filed on Apr. 13, 2012 by Shiber and entitled "ROTARY CATHETER FOR OPENING OBSTRUCTED BODILY VESSELS"; as well as 3) U.S. Provisional Pat. Appl. 61/998,138 filed on Jun. 18, 2014 by Shiber and entitled "PHARMACEUTICAL-MECHANICAL SYSTEM FOR OPENING OBSTRUCTED BLOOD VESSELS". All the disclosures contained in the above patent applications and provisional patent applications are incorporated herein by reference in their entireties.

FIELD OF THE INVENTION

This application relates rotary catheters and methods using mechanical and pharmaceutical means for opening partially and totally obstructed bodily vessels of varying diameters such as blood vessels and to a rotary catheter drive unit containing seal-sets working in conjunction with a flexible shaft.

BACKGROUND OF THE INVENTION

Prior art mechanical devices are often limited to treating a narrow range of vessel diameters and a certain type of obstruction. However, the diameter and the nature of the obstruction often varies along the diseased vessel, requiring multiple sizes and different kinds of prior art devices in a single clinical case. Furthermore, each of such prior art devices can be slow, traumatic and expensive. For example, a number of prior art devices comprise an abrasive tip with a spherical cross section, mounted on a rotating shaft to grind the obstructions to very small particles that can pass through the capillary blood vessels. Due to the small size of the particles, these devices have to be rotated at high speeds (e.g., 200,000 revolutions per minute) to grind the entire obstruction material in a reasonable time. In some of these devices, the tip is eccentrically mounted on the shaft and some of these devices use aspiration to try to remove the particles. However, as the abrasive tip of these devices grinds through a small vessel or through a hard obstruction material, even if the tip is mounted eccentrically on the shaft, it is forced to rotate in an opening that is not larger than the tip, which the tip essentially blocks. This prevents aspiration and cooling fluid or drugs from reaching the sides and the distal end of the tip, which may quickly cause thermal injury and/or perforation of the vessel wall.

A different commonly used method to open obstructed blood vessels consists of bringing clot-dissolving drugs (e.g., thrombolytic drugs such as streptokinase, urokinase, tPA and the like) into contact with the obstruction. However such drugs may take a long time, especially in the case of a long obstruction. Thus, catheters, which deliver and mix the drug with the obstruction material to accelerate the process, are available (e.g., Trellis System sold by Covidien Co., Mansfield, Mass.), but such systems are relatively cumbersome, expensive and address primarily soft obstructions.

Advantageous Effect of the Invention

By way of comparison, an embodiment of the present invention has an asymmetric narrow tip with sides that are designed to bluntly impact the obstruction to break the obstruction mechanically. The narrow tip also defines passages that deliver cooling/lubricating fluid and drugs to the impact site and allows the dual mechanical and pharmaceutical co-action to quickly break down the obstruction to particles. The same passages allow the tube to aspirate fluid laden with particles.

The tip is rotated by a motor drive having a seal-set containing a bearing defining a bore and a seal defining a bore and mounted adjacent to the bearing with the bores concentric relative to one another.

The motor has an output shaft that is power transmittingly and concentrically connected to a flexible shaft which passes through the seal-set and has a diameter smaller than the bearing bore and larger than the seal bore.

Ideally, the flexible shaft and the two bores would be concentric. However, due to inherent manufacturing tolerances of the drive assembly parts, this is rarely if ever the case. Therefore, the flexible shaft, when passing through the bearing bore, is deflected by the bearing bore to be aligned (i.e. concentric) with and to interferencingly fit through the seal bore and hydraulically seal the seal bore.

SUMMARY OF THE INVENTION

The present invention discloses a motor drive for a rotary medical device having at least one seal-set which comprises, in combination, a bearing defining a bore, a motor having an output shaft, a flexible shaft having a diameter smaller than the bearing's bore and being power transmittingly and concentrically connected to the output shaft, a seal defining a bore that is smaller than the flexible shaft's diameter and which is mounted adjacent to the bearing with the seal's bore concentric relative with the bearing's bore. The flexible shaft passes through the bearings bore which sufficiently deflects it to be aligned with and to interferencingly fit through the seal's bore and hydraulically seal the seal's bore.

BRIEF DESCRIPTION OF THE DRAWINGS

FIG. 1c shows a cross-sectional enlargement of a connection between a ferrule and flexible tube viewed on a plane 1c-1c marked on FIG. 1a.

FIG. 3 shows a distal end of the tip viewed on plane 3-3 marked on

FIG. 2.

FIG. 10a shows an overview of a modified rotary catheter with a torus-shaped seal-sets located adjacent to a bearing and a flexible tube shielding the tip.

FIG. 10b shows an end view of the rotary catheter as viewed on a plane 10b-10b marked on FIG. 10a.

Figure 1:
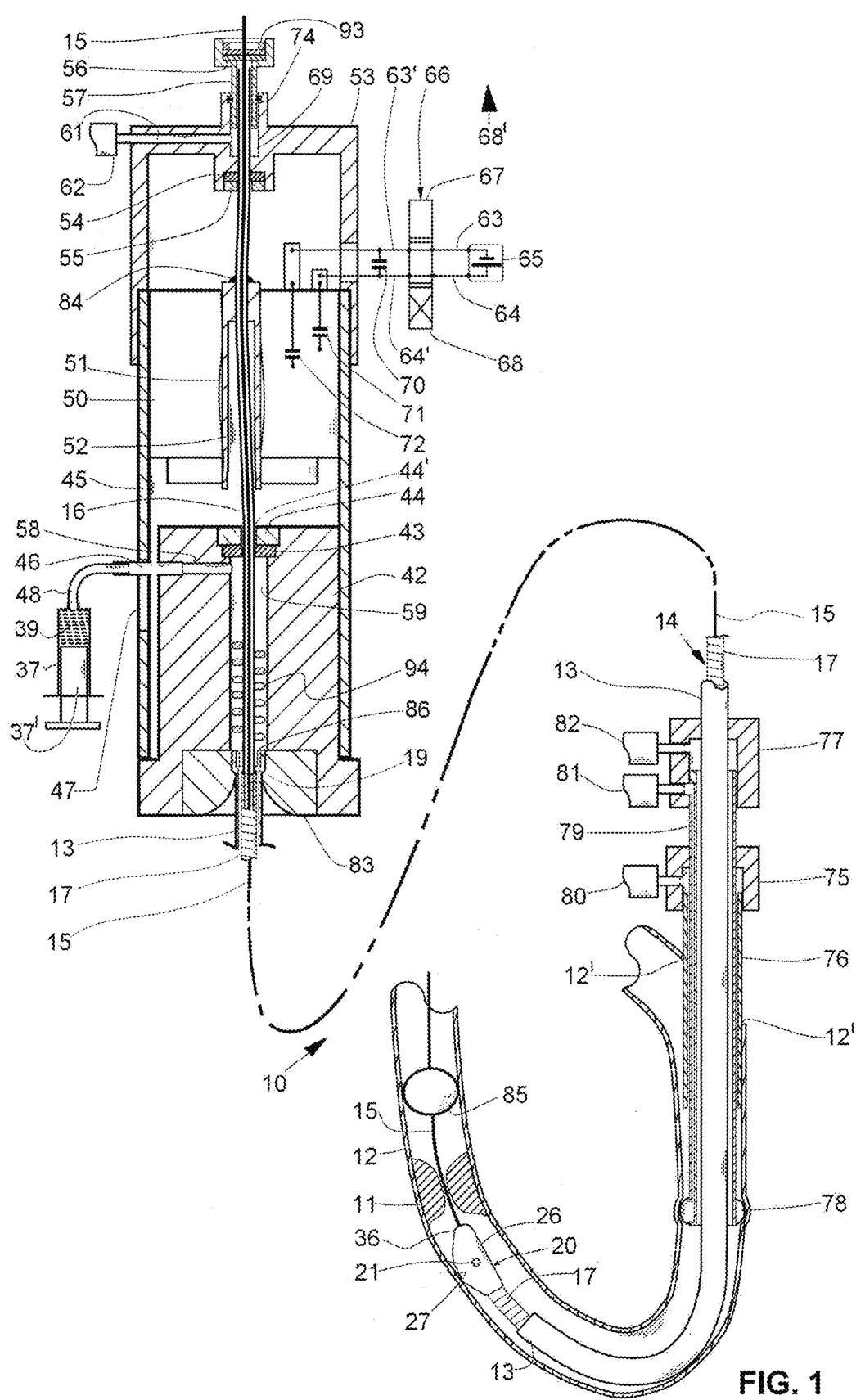
FIG. 1 shows a motorized rotary catheter containing motor drive with two seal-sets according to the present invention.

NOTE: The middle portions of the embodiments shown in FIGS. 1, 1a, 10, 10a, 11, and 12 have been represented by phantom lines due to space limitations on the drawing sheets.

DETAILED DESCRIPTION OF THE INVENTION

The rotary catheter can be inserted into a vessel directly, e.g., when access to a vessel is gained surgically, or through the skin via an introducer. The introducer can also be used to inject fluids, such as saline, with drugs and radiopaque contrast agent into the vessel, which, together with blood, keeps the obstruction particles suspended so that they can be readily aspirated. An optional guiding catheter can be used when the rotary catheter has to be guided further into the vessel. The guiding catheter can incorporate a proximal embolic barrier for temporarily blocking flow through the vessel, while the rotary catheter macerates and aspirates the obstruction material, thereby reducing the likelihood of releasing particles and drugs downstream. A distal embolic protection device can also be employed for the same purpose and, when the rotary catheter is used in a limb, an external pressure cuff can be utilized to temporarily stop circulation in the affected limb.

The flexible hollow shaft that is disposed in the flexible tube deters the flexible tube from kinking (i.e., diametrically collapsing) and prevents the flexible hollow shaft and tube from being sharply bent at the point in which they are connected to the housing. Their radii of bending is limited by a radius of curvature of a wall of a depression defined by the surrounding housing. The rotary catheter can be manufactured in varying lengths and diameters to reach and treat different anatomical locations and different forms of obstructions, as well as to suit users' preferences.

Each of the seal-sets comprises a bearing defining a bore larger than the flexible shaft's diameter, a seal defining a bore that is smaller than the flexible shaft's diameter, the seal being mounted adjacent to the bearing with the two bores being concentric.

FIG. 1 shows a motorized rotary catheter 10, according to the present invention, for opening an obstruction 11 (e.g., blood clot; atheroma) in a bodily vessel 12 (e.g., a blood vessel). FIG. 1 further shows a rotary catheter's drive unit utilizing a motor with a hollow output shaft. The output shaft is connected to a hollow flexible shaft that is concentrically nested in it.

Proximal and distal ends of the flexible shaft extend out of the motor's output shaft and rotatably pass through a proximal seal-set (which comprise bearing 55 and seal 54) and a distal seal-set (which comprise bearing 44 and seal 43).

The motor 50 is practically always misaligned relative to a cylinder 42 and a proximal cap 53 (and to illustrate, it is shown shifted leftwards in FIG. 1) due to spacing between the parts and due to production tolerances of the parts) and, to address this misalignment each of the flexible shafts' ends is sufficiently deflected by the bearings' bores to aligns the shaft's end with the associated seal's bore through which it interferencingly fits to hydraulically seal the bore.

Figure 1A:
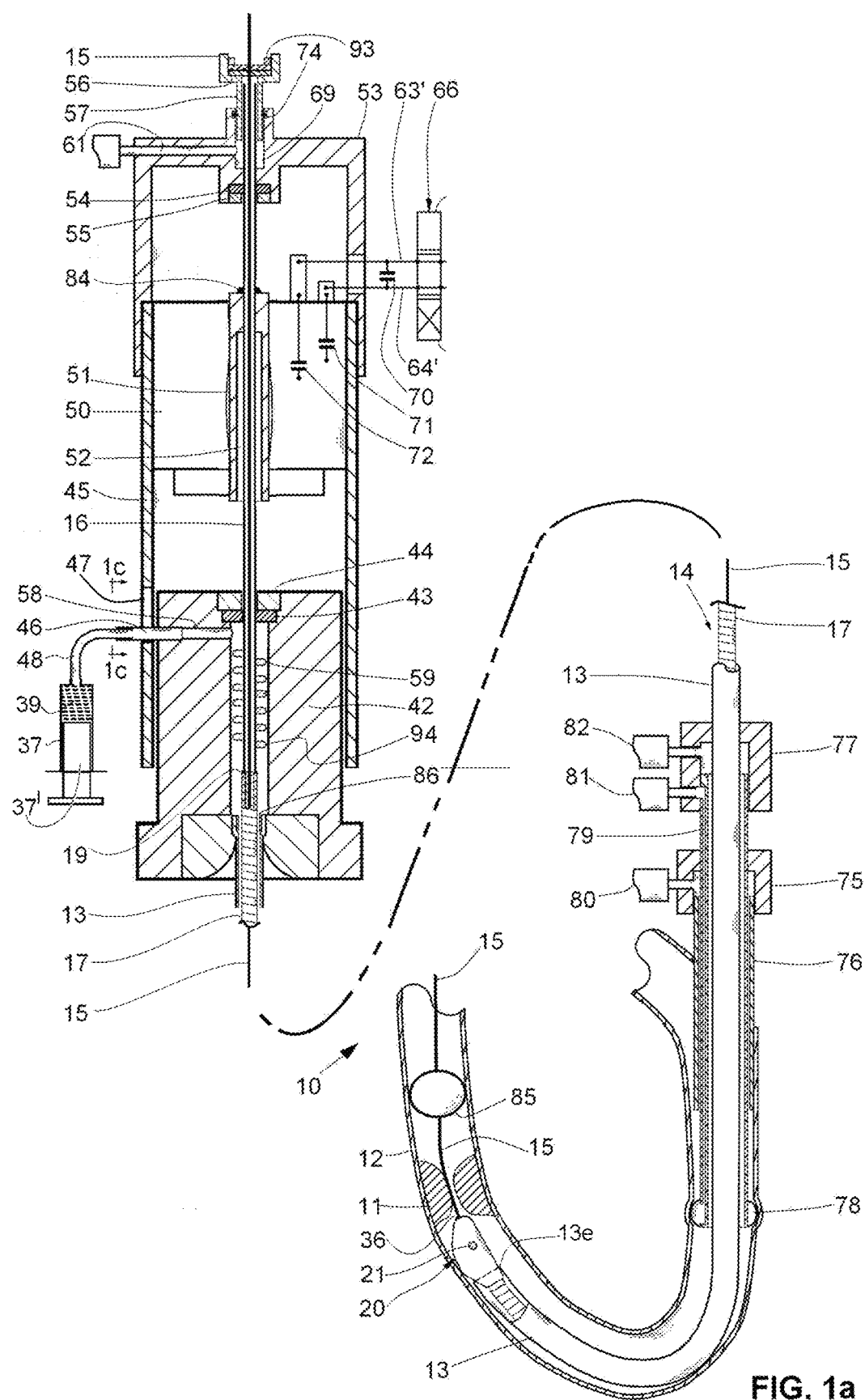
FIG. 1a shows one embodiment of a motorized rotary catheter for use with the present invention, with a proximal seal in a closed position.
Figure 1B:
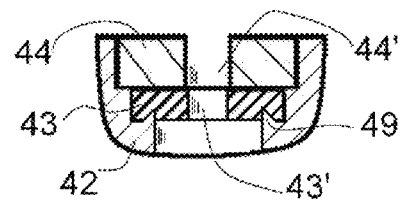
FIG. 1b shows and enlargement of a rotary seal-set.
Figure 1C:

FIG. 1a shows the motorized rotary catheter with the distal end of its flexible tube slid close to the tip to reduce a gap between them and impede an edge of the flexible tube from engaging with a wall of the vessel while the rotary catheter is advanced distally in the vessel towards an obstruction ("distal" or "distally" refers to a location or a direction further into the vessel and "proximal" or "proximally" means the opposite). FIG. 1c shows cross-sectional enlargement of a connection between a ferrule and flexible tube viewed on a plane 1c-1c marked on FIG. 1a.

The rotary catheter 10 comprises a motor-driven flexible hollow shaft 14, rotatably disposed in a flexible tube 13 that is preferably made of thin plastic material. A proximal portion 16 of the flexible hollow shaft is preferably a thin-walled tube and a distal portion of the flexible hollow shaft 17 is preferably made of a spiraled wire. The wire that is used to wind the spiraled wire preferably has a flattened cross-section (such a cross section can be obtained by taking a standard round wire and running it between rollers that squeeze and flatten it, please note FIGS. 4, 5 and 6.) The flexible hollow shaft portions 16 and 17 are preferably made of metal (e.g., stainless steel; Nitinol) and are connected together, for example, by a circumferential weld 19 (please note FIG. 1) or by two circumferential welds 124 and 125 and a reinforcing sleeve 30 (please note FIG. 7.)

Figure 9:
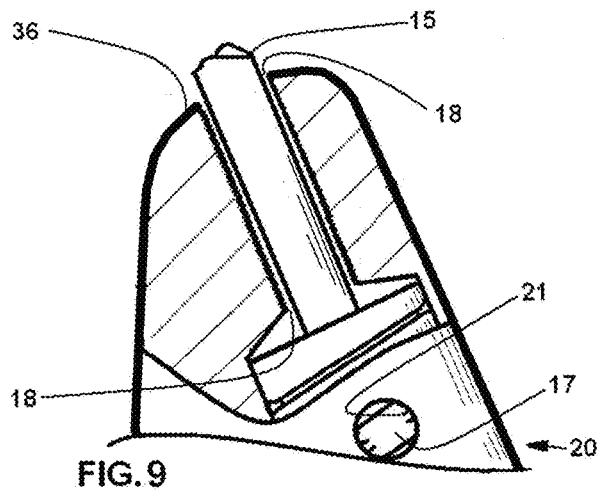
FIG. 9 shows a further enlargement of the distal end of the tip.

A stainless steel tip 20 is affixed by a laser weld 21 to a distal end of the spiraled wire (please note FIG. 9) so that the flexible hollow shaft 14 and the tip 20 are rotatable and slideable over a guidewire 15. The weld 21 is at a point along the spiraled wire that is nested inside the tip where the weld is subjected primarily to shearing loads but is otherwise protected. The tip has a first side 22 for impacting the obstruction as the flexible hollow shaft is rotated in a first direction 40. A second side 24 can be used to impact the obstruction if the flexible hollow shaft is rotated in a second direction 41 (please note FIG. 3.)

Figure 3A:
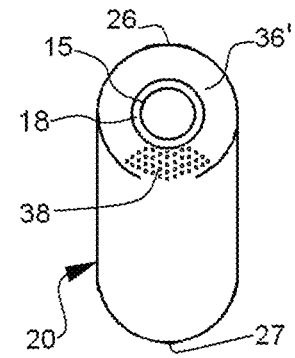
FIG. 3a shows a distal end of a modified tip.
Figure 3:
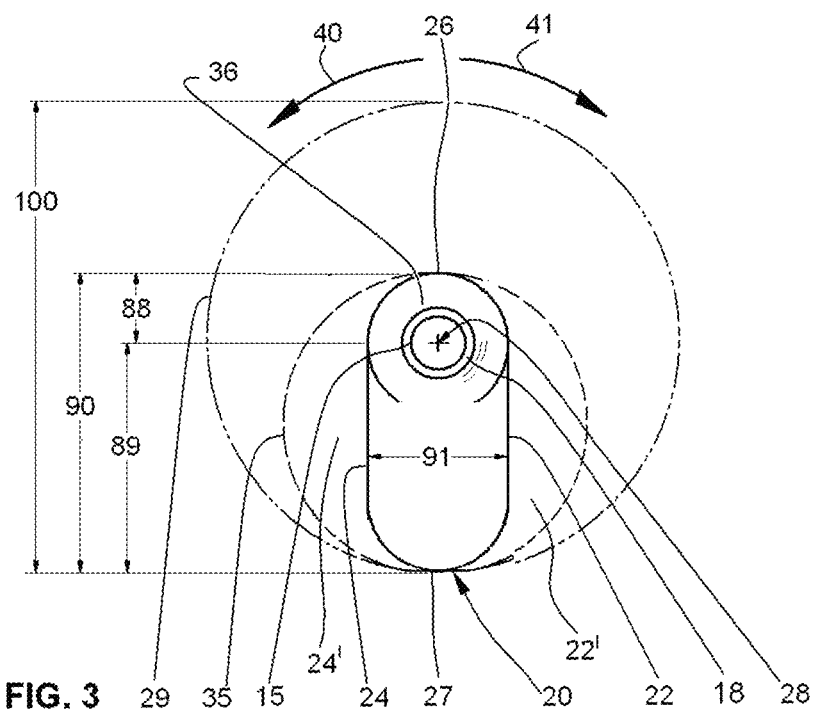

The tip also has a base 26 and an opposing crown 27 that is adapted to atraumatically slide against a wall of the vessel without injuring it. The tip 20 is asymmetrical, i.e., an offset 89 of its crown is larger than an offset of its base 88. "Offset" refers hereinafter to a distance from the longitudinal axis 28 of the spiraled wire 17. The sum of offsets 88 and 89 equals to the height of the blade 90 and the offset 89 is also the tip's "effective radius" i.e., one half of its "effective diameter" 100. As the tip rotates around the axis 28, the crown slides along its surroundings while the side of the tip impacts whatever is within its effective diameter marked with a phantom line 29 and, as illustrated in FIG. 3, the resulting tunnel is substantially larger than a tunnel marked with an interrupted line 35 that a hypothetical symmetrical tip of equal height (i.e. offset 88 equals offset 89) would have opened, however, it should be understood that above discussion is meant to explain the concept of the asymmetrical tip and the actual cross-sectional area of the tunnel that the tip 20 opens may increase due to, for example, dynamic forces affecting the tip (e.g., centrifugal force) or the opening may decrease when, for example, the tip operates in a smaller vessel or when it tunnels through a hard obstruction.

The tips narrowed cross-section with a width 91 that is smaller than its height 90 reduces the size and circumference of the cross-section relative to a round tip whose diameter equals the height. This smaller circumference requires a smaller opening in the wall of the vessel for inserting the tip into the vessel. The narrowed cross-section also enhances the tip's ability to fit into a narrow opening in a hard obstruction and, as the tip rotates, to apply leverage in order to widen the opening. The tip's narrowed cross-section also leaves open passageways 22' and 24' along its sides 22 and 24, respectively. These passageways enable aspiration from the distal end of the flexible tube 13 to reach particles that are distal to the tip even when the tip is operating in a small vessel or tunnel with a diameter as small as the height 90. As the particles and fluid in which they are suspended pass through passageways 22' and 24', over the rotating tip, they become further macerated and are readily aspirated through the tube into a syringe 37 as discussed below.

Figure 2:
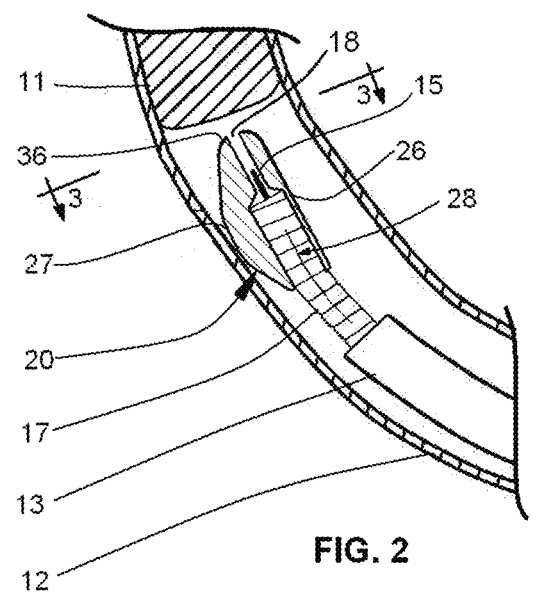
FIG. 2 shows an enlargement of a region marked 2 on FIG. 1, where the vessel is totally occluded and the guidewire withdrawn proximally beyond the distal end preparatory to the tip crossing the obstruction.
Figure 8A:
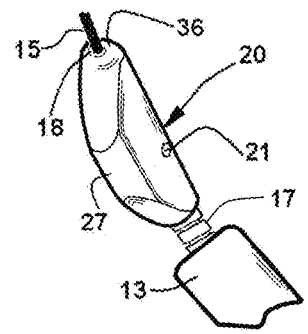
FIG. 8a shows a perspective view of the tip.
Figure 8:
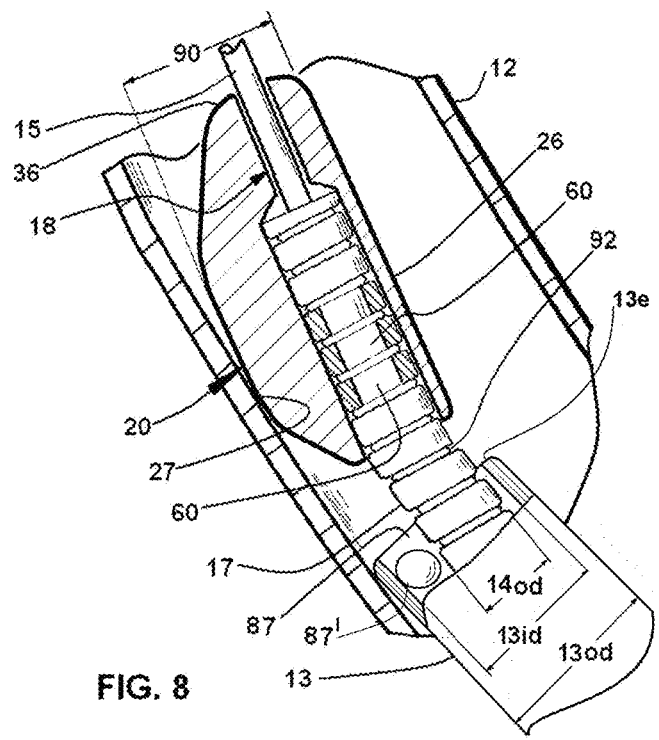
FIG. 8 shows an enlarged cross section of the tip area.
Figure 8B:
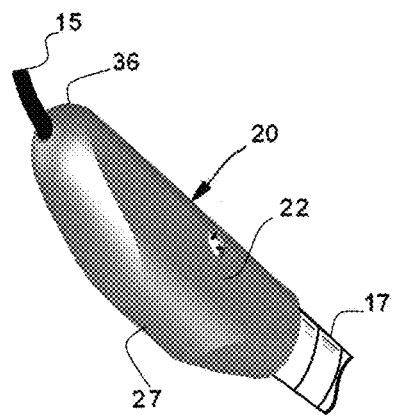
FIG. 8b shows a perspective illustration of the tip.

A distal rounded end 36 of the tip 20 covers a distal end of the spiraled wire and defines a bore 18 (please note FIGS. 2, 8 and 9) which rotatably and slideably fits over the guidewire, enabling the guidewire to support and guide the tip. A close fit between bore 18 and the guidewire restricts blood flow through the bore 18 and the amount of fibers and residue that enters through the bore 18 and may deposit around the guidewire.

As shown in FIG. 1 the flexible tube 13 is affixed (e.g., bonded and/or press fitted) and radially supported internally by a ferrule 86, to a strain relief 83 which is affixed to the cylinder 42 which also houses a seal 43. The outer periphery of the seal 43 is tightly pressed by a bearing 44 against a circular ridge 49 forming a peripheral static seal (please note FIG. 1b which shows an enlarged view of a seal-set.)

Figures 10, 10C:
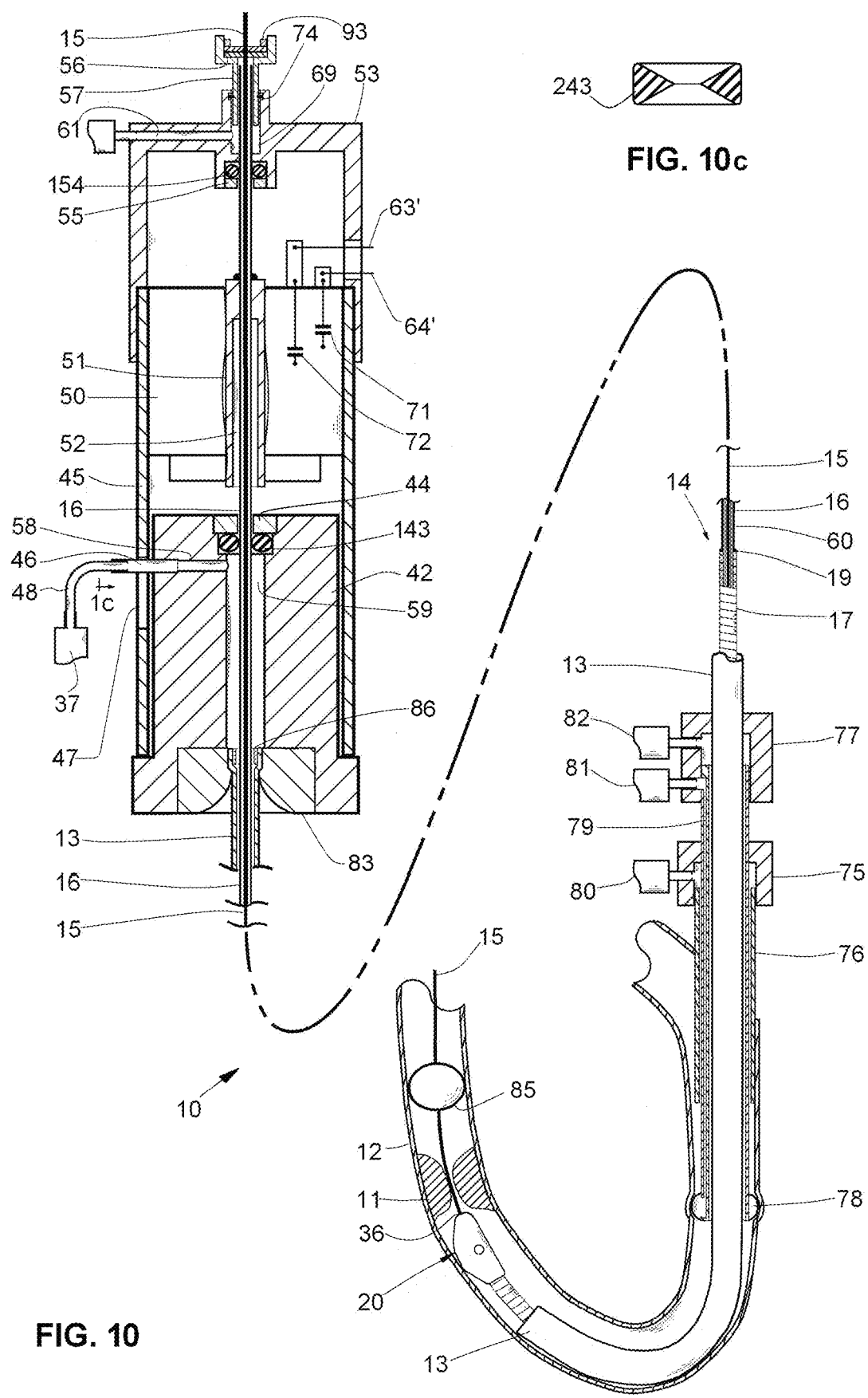
FIG. 10 shows a motorized rotary catheter containing motor drive with two seal-sets where the seal is torus shaped O-ring.
FIG. 10c shows a seal with an alternative triangular cross-section (toroid) in place of a torus.

A bore 44', defined by the bearing 44 offsets (or bends) the flexible hollow shaft portion 16 to the extent that is needed to concentrically align it relative to a bore 43' which is defined by the seal 43 (such a combination of a seal and an adjacent concentric bearing are referred to herein as a "seal-set".) This alignment, as would be understood by one skilled in the art, nulls the misalignment between parts 43' and 16 caused by the cumulative eccentricities and production tolerances of parts numbers 42, 45, 50, 51, 83 and 16 and, it reduces the interference fit needed to maintain the seal between the parts 43'. This has a cascade of beneficial effects as the lower interference lowers the frictional power losses in the seal and therefore the needed motor's power output. This in turn lowers the maximum torque that the flexible spiraled shaft 17 may be subjected to and allows using a less rigid and less injurious flexible spiraled shaft 17. Further, lowering the required tolerances that the parts 42, 45, 50, 51 and flexible hollow shaft portion 16 have to be manufactured to lowers their cost. An alternative seal-set is shown in FIG. 10, where the seal 154 is a torus shaped O-ring made of an elastomeric material located adjacent to the bearing 55 and seal 143 is a torus shaped O-ring made of an elastomeric material located adjacent to the bearing 44. FIG. 10c shows another alternative toroidal shaped seal 243 with a triangular cross-section in place of a torus.

Figures 10A, 10B:
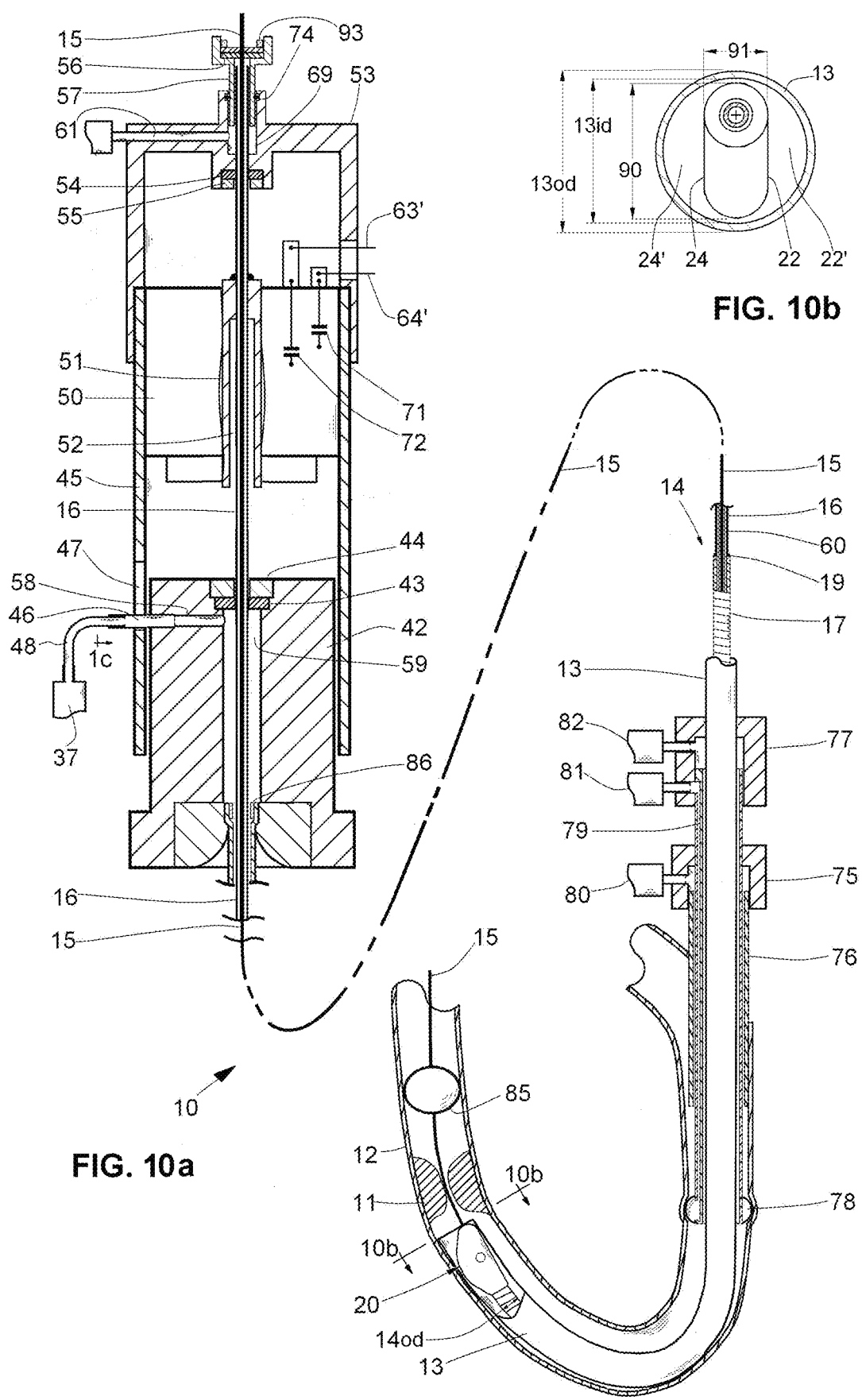

The flexible tube can be optionally moved distally over the tip to shield it, as shown in FIG. 10a. FIG. 10b shows an end view of the rotary catheter as viewed on a plane 10b-10b marked on FIG. 10a.

The cylinder 42 is slidingly disposed in a distal end of a tubular housing 45 and a ferrule 46, that is press-fitted into the cylinder 42, and is slidingly disposed in an elongated slot 47 defined in the housing 45. This allows the cylinder 42 to be slid proximally into the housing (as shown in FIG. 1) or to be slid distally (as shown in FIG. 1a), displacing the distal end of the flexible tube 13 towards the tip 20. The reduced gap impedes the edge 13e from engaging with the wall of the vessel 12. While the edge 13e is preferably rounded or chamfered (please note FIG. 8), the reduced gap further reduces the likelihood that the edge 13e would scrape the wall of the vessel 12 while the rotary catheter is advanced distally in a curved section of the vessel.

A flexible conduit 48, the ferrule 46, bores 58 and 59, and seal 43 (please note FIG. 1) define together a hydraulic connection between a proximal end of the flexible tube 13 and a suction means in the form of the syringe 37. The syringe has a piston 37' and a cylindrical body which contains thrombolytic drug(s) 39, such as, for example, streptokinase, urokinase, tissue plasminogen activators, also referred to as tPA or rtPA and may also contain anticoagulant and antispasmodic drugs. Typical thrombolytic drugs are sold by, for example: Genentech, South San Francisco, Calif.; Abbott Laboratories, Green Oaks, Ill.; AstraZeneca, London, UK. The drugs maybe infused into the vessel 12 before and/or while the tip is rotating by pushing the piston 37' into the syringe's cylindrical body. After the thrombolytic drug and the tip have cooperatively broken down the obstruction 11 to particles small enough to be aspirated into the fluid channel defined between the tube 13 and the shaft 14, the piston 37' is pulled out of the cylindrical body to create a negative pressure in the syringe and aspirate the particles and fluid in which they are suspended. Representative syringes and vacuum syringes are sold, for example, by Merit Medical Systems, South Jordan, Utah. The relative motion between the flexible tube 13 and the rotating flexible hollow shaft 14 assists with the aspiration process by reducing the frictional resistance that these particles encounter while moving proximally in the flexible tube 13.

An optional helical wire 94 can be rotatably disposed in bore 59 and affixed to the flexible hollow shaft portion 16. Upon rotation in the first direction, the helical wire 94 automatically assists and regulates flow of fluid and particles proximally, but when not rotating, the helical wire 94 resists such flow.

A small direct current motor 50 is housed in a proximal end of the housing 45, however, other types of electric or air-driven motors, and the like, can be used. The motor has a tubular second bore 51 with an optional electrically insulating coating (not shown.). The shaft 51 is power transmittingly connected at its proximal end to the flexible hollow shaft portion 16 by a circumferential weld 84 (or, alternatively, by epoxy which is not shown), leaving the length of flexible hollow shaft portion 16 that is nested in a clearance 52 free to bend and align with the bore 44'. The increased length of flexible hollow shaft portion 16 that participates in bending and alignment with bore 44' lowers the stress and strain in the flexible hollow shaft and the frictional forces that develop in the bore 44' while the flexible hollow shaft portion 16 rotates in its bent configuration shown in FIG. 1.

Figure 7:
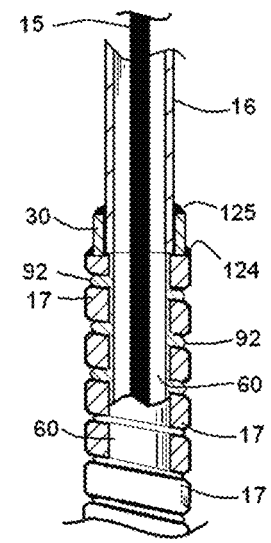
FIG. 7 shows an enlargement of an optional welded connection between a flexible hollow shaft portion and spiraled wire.

FIG. 7 shows the flexible hollow shaft portion 16 connected and bonded to an optional flexible guidewire-liner 60 made of a thin-walled plastic tube. The liner may also be secured to the spiraled wire 17 with a spiraled protrusion 92 formed thereon. The spiraled wire can be wound of one or more wires, also referred to by various manufacturers as strands or filaments, and it can be constructed in one or more layers of wound wires. Representative single and multi-layered spiraled wires are disclosed in U.S. Pat. Nos. 4,819, 634 and 5,007,896, which are incorporated herein by reference. These earlier patents also show other optional spiraled wire designs, such as a jagged spiraled wire shown in FIGS. 3 and 4 of U.S. Pat. No. 5,007,896. Torque-transmitting flexible tubes utilizing a single or multilayered construction, where each layer is made of one or more wires, are also commercially available from Asahi Intecc Co. (with offices at 2500 Red Hill Ave, Santa Ana, Calif., USA and at Aichi-ken, Japan.). The common feature of these and other suitable spiraled wires, as the term is used in this application, is their hollow design which allows them to slide and rotate over a guidewire, coupled with an ability to transmit torque from the motor to the tip and their increased flexibility, as compared with a non-spiraled or a standard tube of similar internal and external diameters.

Figure 1D:
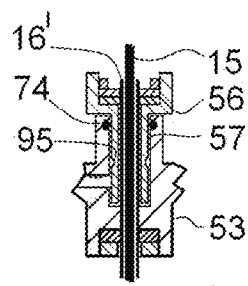
FIG. 1d is a cross-sectional view of a proximal seal mechanism shown in an open position.

Referring back to FIG. 1, the proximal cap 53 houses a seal-set comprising a seal 54, which seals around the flexible hollow shaft portion 16, and a bearing 55 which secures the seal 54 in place, and keeps the flexible hollow shaft portion 16 rotating concentrically relative to the seal 54 with the beneficial effects discussed above in connection with the bearing 44 and the seal 43. Housing 45, cylinder 42 and proximal cap 53 are all parts of the rotary catheter drive unit. The cap 53 also defines a bore containing an O-ring seal 74 through which a slideable proximal extension in the form of a stepped tube 57 is slidingly disposed. A seal 56 is secured in the stepped tube 57 by a ring 93. To enable insertion of the guidewire 15 thru the rotary catheter 10, the stepped tube 57 is pushed distally, causing a proximal end 16' of the proximal flexible hollow shaft portion 16 to cross the seal 56 (please note FIG. 1d) and enable the guidewire to freely pass thru the seal 56 into, or out of, the proximal end 16'. Upon pulling the stepped tube 57 proximally (please note FIG. 1), the seal 56 closes and seals around the guidewire 15. The seal 56 may be made of more than one layer of elastomeric material (e.g., two layers of flat silicone rubber), where the distal layer defines a round bore that tightly, yet slidingly, fits around the guidewire 15. The proximal layer has a slit, or intersecting slits, that seal hermetically in the absence of the guidewire. The O-ring 74 seals around the stepped tube 57 and frictionally prevents it from rotating. It also provides the user a tactile indication, when it drops into an undercut 95 (please note FIG. 1d), that the stepped tube 57 is in its extended position. FIG. 1d is cross-sectional view of a proximal seal mechanism shown in an open-position (the proximal seal is shown, as a part of the embodiment depicted in FIG. 1, in a closed-position).

Figure 1E:
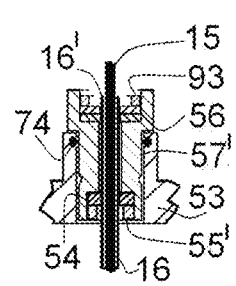
FIG. 1e is cross-sectional view of an alternative proximal seal mechanism shown in an open position.

FIG. 1e is cross-sectional view of a modified slideable proximal extension means in the form of a stepped tube 57' which defines a bore that provides a bearing support and concentric alignment for the flexible hollow shaft portion 16 with both seals 54 and 56 that are housed and secured at the distal and proximal ends of the stepped tube 57', respectively. Therefore, the bore of bearing 55' can be enlarged. Stepped tube 57' is depicted being pushed distally to a position that enables the guidewire to freely pass distally or proximally thru the distal end 16'. Upon pulling the stepped tube 57' proximally, the seal 56 closes and, if a guidewire is present, seals around the guidewire. In this modified configuration shown in FIG. 1e, the O-ring 74 provides anti-rotational friction and tactile indication discussed above.

A syringe 62 is hydraulically connected to a proximal end of the flexible hollow shaft portion 16 through a passage 61 and a bore 69 defined in the cap 53. The syringe 62 can be used to introduce a fluid, such as saline and/or drugs, into the flexible hollow shaft portion 16 and into the liner 60 to prevent blood from entering and clotting in the liner and in the flexible hollow shaft portion 16. Immersion of the proximal end of flexible hollow shaft portion 16 in fluid also prevents air from entering into it when negative pressure prevails in bore 69. The fluid can be supplied by the syringe 62.

Electrical wires 63, 63', 64 and 64' connect the motor 50 to a battery 65 through a four position switch 66 having a sliding block 68. In the position shown in FIG. 1, wire 63 is connected to wire 63' and wire 64 is connected to wire 64', causing the motor to rotate in the first direction. When the block 68 is slid upwards (in the direction of arrow 68'), the wires are crossed so that wire 63 is connected to wire 64' and wire 64 is connected wire 63', causing the motor to rotate in the second direction and manually alternating between these positions will cause the motor to rotate back and forth. When a block 67 is slid downwards an electronic circuit that it contains is interposed between the wires 63 and 64 to the wires 63' and 64' which automatically causes the motor to rotate back and forth (such electronic circuitry which is not shown is familiar to the artisan.) In a fourth off-position (not shown) the switch electrically disconnects the battery from the motor.

Motor 50 has a commutator which can be equipped with a disk varistor to reduce electromagnetic emissions (disk varistors are commercially available, for example, from TDK Corp., Uniondale, N.Y.) Additionally capacitors 70, 71 and 72 can be connected to a housing of the motor and wired as shown in FIG. 1.

Ferrite beads (not shown) can be disposed along the wires 63, 64 and 63', 64' to further reduce the electromagnetic emissions.

A syringe 80 is connected through an introducer 75 to the vessel and can be used for the introduction of a fluid, such as saline, drugs and radiopaque contrast agent, into the vessel. This fluid can make up for the volume that is aspirated through the rotary catheter and can be used to prevent blood from entering the introducer and clotting therein. Alternatively, the syringe 80 can be used to aspirate fluid and particles out of the vessel, especially while the rotary catheter 10 is not disposed in the introducer.

In cases where the target obstruction 11 is distant from the puncture site, a conventional guiding catheter (not shown) may be disposed in the introducer, to guide the rotary catheter 10 more definitively to the obstruction. Alternatively, a specialized catheter 77 with a toroidal shaped balloon 78 can be used to also seal flow through the vessel and reduce the likelihood of escapement of particles and drugs into the blood stream. The balloon 78 is inflatable and deflatable through a channel 79, defined in a wall of the catheter, by a syringe 81 that is connected to the channel 79.

A syringe 82 can be used similarly to syringe 80. While syringes 62, 80, 81 and 82 are illustrated as being connected directly to various other components, it is understood that they can be connected through flexible conduits similar to the way syringe 37 is connected through flexible conduit 48. It can be noted that syringe 82 or syringe 80 can be replaced with a bag containing a fluid preferably under pressure slightly higher than the patient's blood pressure (not shown).

The guidewire 15 can be a conventional guidewire or it can be equipped with a distal particle barrier such as a filter (not shown) or a balloon 85 that is selectively inflatable through the guidewire 15. Such guidewires with inflatable balloons are commercially available from Medtronic Co., Minneapolis, Minn.

Bodily vessels are often curved and bias a catheter that is inserted into them towards the wall of the vessel. Absent a correction mechanism, such a bias would lead tunneling catheters (i.e., catheters that are intended open an obstruction) to begin tunneling into the obstruction adjacent to the wall, especially in a case of an obstruction that totally blocks the vessel and cannot be crossed by the guidewire. In such a case the rotary catheter 10 can be delivered to the vicinity of the obstruction site over the guidewire. The guidewire is then withdrawn proximally past the distal end 36 of the tip. Then, as the tip 20 rotates and the crown 27 atraumatically slides against the wall of the vessel, it displaces the distal end 36 of the tip away from the wall (please note FIG. 2.), urging the distal end of the tip to start tunneling away from the wall. After the obstruction has been crossed by the tip 20, the guidewire can be advanced distally beyond the obstruction, and it can be left inside the vessel after the rotary catheter has been withdrawn, to provide guidance for subsequent procedures, such as angioplasty and stenting. It can be understood by the artisan that this correction mechanism of starting to tunnel away from the vessel's wall would not work if the flexible hollow shaft 14 would hypothetically extend distally beyond the tip's distal end 36, as the tip could not have remotely prevented such a distal extension of the flexible hollow shaft from starting to tunnel adjacent to the wall. Such a distal extension of the flexible hollow shaft would have also increased the force that would have developed between the rotating crown and the wall of the vessel because, as would be appreciated by the artisan, larger force has to be applied at a mid-point of a beam supported at both of its ends as compared with the force that has to applied at the end of a cantilevered beam in order to cause the same deflection.

Total obstructions may have a hard end layer thus, to enable the tip to start tunneling, its rounded distal end 36' can have small tooth or teeth 38 on the part of the distal end of the tip that is further away from the base 26 (please note FIG. 3a) to reduce the likelihood that teeth 38 will come into contact with the vessel. To prevent or to release fibers and the like from wrapping around the flexible hollow shaft or the tip, the flexible hollow shaft and tip can be rotated backwards or back and forth in directions 40 and 41. Additionally, in the event that a large particle becomes lodged in the tube, sliding the flexible tube 13 back and forth relative to the flexible hollow shaft 14 can be used to help dislodge it.

The rotary catheter can be introduced into the vessel directly, when the vessel is surgically accessed, or percutaneously through an introducer 75, having a sheath 76. The size of an allowable puncture wound 12' (note FIG. 1) in the vessel wall limits the diameter of the sheath 76 and an outside diameter 13od of the flexible tube 13 and the size of the inner workings of the catheter and of the tip 20. The flexible tube's internal diameter 13id and an outside diameter 14od of the flexible hollow shaft 14 (please note FIG. 8) define between them a fluid channel 87. To maximize the cross sectional area of the fluid channel 87 and the size a particle 87' that the fluid channel can ingest, the sheath 76 as well as the flexible tube 13 are preferably made of a thin plastic materials and a diameter 14od of the flexible hollow shaft is kept substantially smaller than the diameter 13id. The distal end of the flexible hollow shaft 14 extends out of a distal end of the flexible tube 13 and is free to move radially relative to the tube, to one side or another, enabling the channel to ingest particles which measure across up to a difference between the diameters 13id to 14od. It should be noted that, if the distal end of the flexible hollow shaft 14 was mechanically connected to and centered in the distal end of the flexible tube 13, for example, by a bearing, the particle size that could have theoretically entered the channel 87 would have been reduced by ½ and the particle weight by about ⅞. As the tip rotates, the interaction of the tip with its surroundings and dynamic forces may cause the distal end of the flexible hollow shaft to randomly move radially or vibrate relative to the tube, which further discourages particles from clogging the fluid channel. Again, by comparison, if the distal ends of the flexible hollow shaft and the flexible tube were mechanically connected by a bearing or the like, not only could such a connection interfere with flow through the channel, it would also diminish the vibratory unclogging action referred to above. It can also be noted that the lack of mechanical connection between the distal ends of the flexible tube 13 and the flexible hollow shaft 14, such as a bearing, for example, enhances the overall flexibility of the rotary catheter by allowing slight longitudinal relative movement between the flexible tube 13 and the flexible hollow shaft 14 when the catheter is bent.

Figure 4:
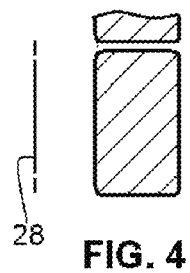
FIG. 4 shows an example of cross sections of flattened wires that can be used to wind a spiraled wire.
Figure 5:
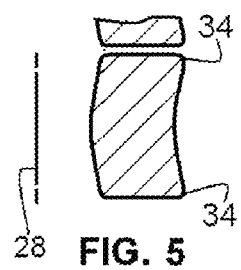
FIG. 5 shows another example of cross sections of flattened wires that can be used to wind a spiraled wire.
Figure 6:
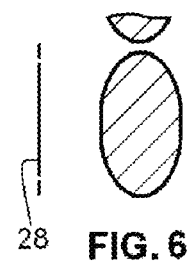
FIG. 6 shows another example of cross sections of flattened wires that can be used to wind a spiraled wire.

If an oversized particle (which measures across more than the difference between the diameters 13*id* to 14*od*) does enter and wedges in the channel 87, the spiraled wire 17 (if one is used) is preferably rotated in a direction that conveys the particle distally to prevent it from lodging in and clogging the fluid channel. This action can be augmented by making the cross section of the wire (from which the spiraled wire is wound) with small external ridges 34 (please note FIG. 5 (for reference, FIGS. 4 and 6 shows other examples of wires' cross sections that can be used to wind a spiraled wire.). However, particles that are small enough not to become wedged in the channel 87 are practically unaffected by the small ridges 34 and are readily aspirated proximally, eased by the relative rotation of the flexible hollow shaft 14 to the flexible tube 13, which substantially reduces the frictional resistance to the movement of particles through the channel 87. Thus, the combined relative rotary and radial motion between the flexible hollow shaft and the flexible tube eases the movement of particles into and through the fluid channel 87 and impedes particles from clogging it.

It can also be appreciated that enlarging the tip's height 90 to closely fit through the introducer enhances its effective radius 89 and the cross-sectional area of the tunnel that the tip opens through the obstruction (please note FIG. 3). Increasing the tip height 90 beyond the flexible tube's internal diameter 13*id* (please note FIG. 8) allows the flexible tube to be advanced to the tip but not over it. The tip's height can be reduced so it is slightly smaller than the internal diameter 13*id*, allowing the flexible tube to be advanced over it and shield it (please note FIGS. 10*a*, 10*b*). In this shielded configuration, the rotary catheter can aspirate soft obstructions (e.g., fresh clot) because the tip's narrowed cross-section leaves open passageways 22' and 24' between the tip's sides 22 and 24 to the flexible tube's wall, respectively. As soon as the soft obstruction material enters the passageways 22' and 24' and gets in between the rotating tip's sides and the flexible tube's wall, the rotating tip and thrombolytic drugs (if used) macerate the clot so that it can be readily aspirated all the way into the syringe 37. The operation of the tip in the tube is similar to the tip's operation in a tunnel or a small vessel whose diameter is close to the tip's height 90.

Figure 11:
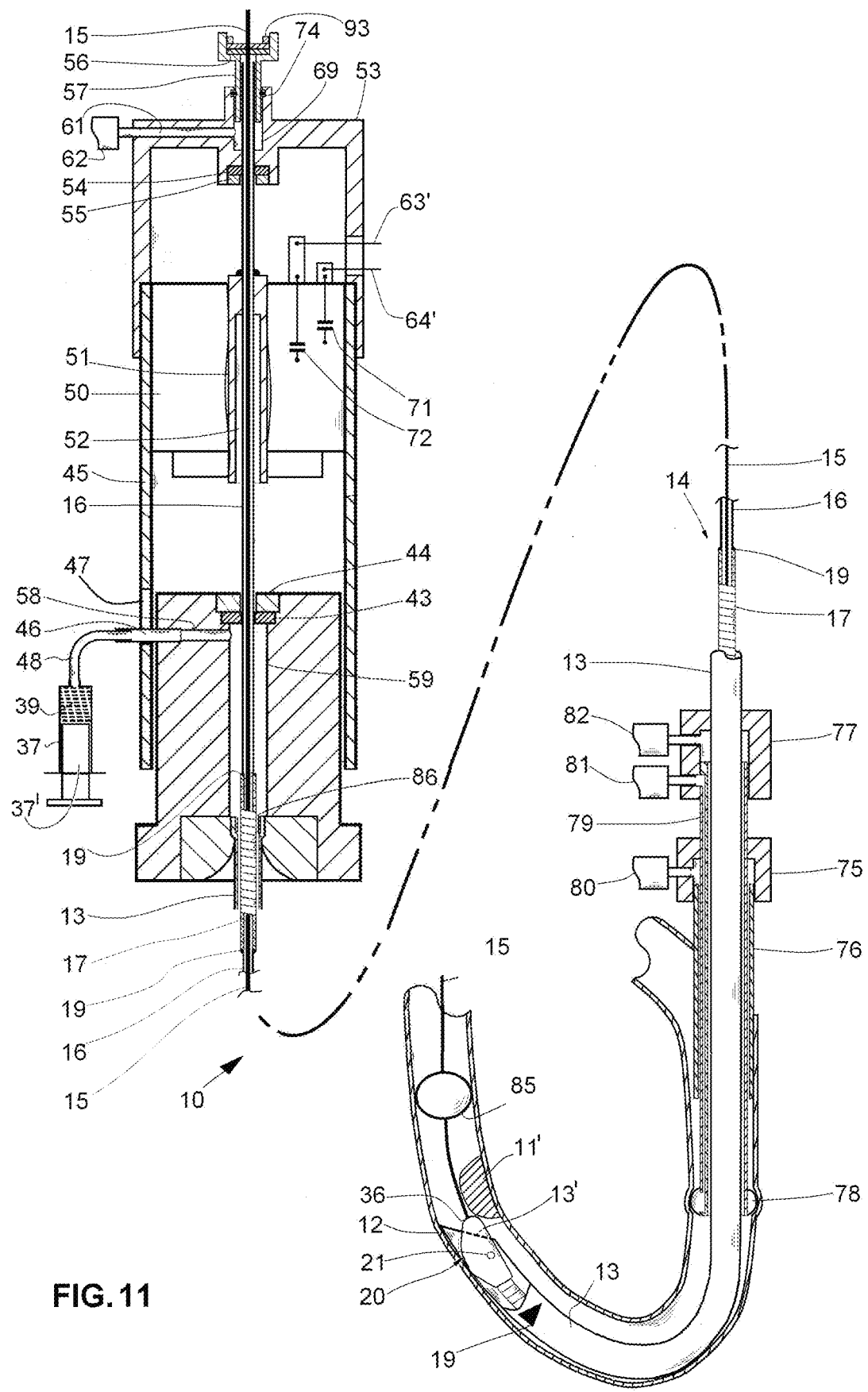
FIG. 11 shows another modification of the rotary catheter, wherein the distal end of the flexible tube is terminated diagonally.

FIG. 11 shows a further modification, where the flexible tube 13 is terminated along a diagonal line 13' so that when the cylinder 42 is partially pulled out of the housing, the flexible tube partially shields the tip. As can be understood by the artisan, the length of the slot 47 can be increased to enable the flexible tube to move from a fully shielding position to a position where the tip and a short section of the spiral are exposed. The configuration shown in FIG. 11 enables the tip to be advanced and urged into contact with an asymmetrical obstruction 11', which is located on one side of the vessel, while the flexible tube distal end acts as a barrier between the tip and an opposite side of the vessel. A radio-opaque marker 19, affixed to the wall of the flexible tube, can be used to assist the user in positioning and orientating the flexible tube relative to the obstruction under X-ray imaging.

Figures 12, 13:
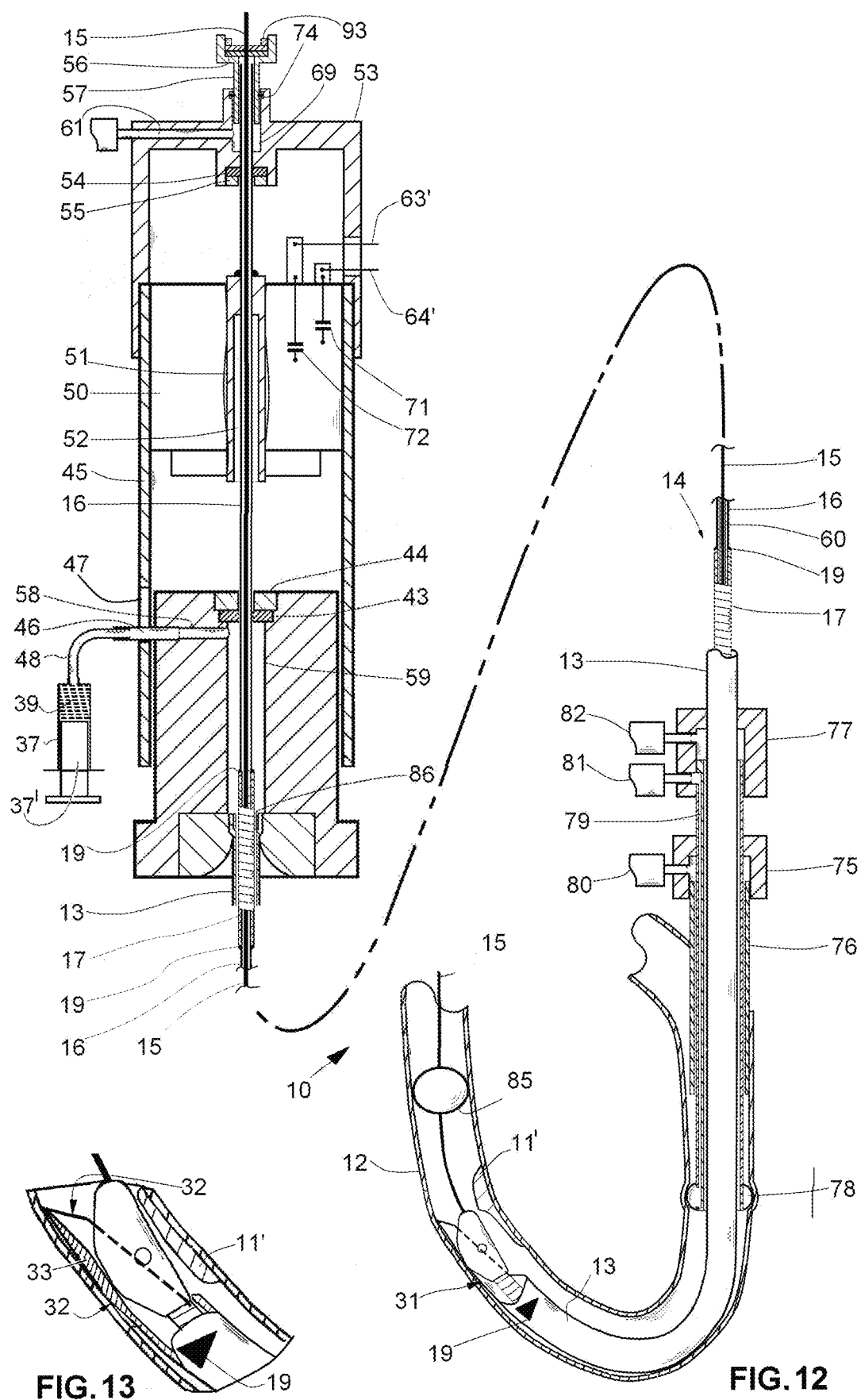
FIG. 12 shows a further modification of the rotary catheter, wherein the shape of the distal end of the flexible tube resembles a scoop of a garden trowel.
FIG. 13 shows a further modification of the rotary catheter, wherein the sheath resembles a scoop of a garden trowel with a thickened bottom.

FIG. 12 shows a modification of the rotary catheter of FIG. 11, where a flexible tube's distal end 31 resembles a miniaturized scoop of a gardening trowel. The scoop shields a certain length of one side of the vessel's wall from the rotating tip while urging the rotating tip towards an asymmetrical obstruction 11' located on the opposite side of the wall. FIG. 13 shows a scoop 32 with a thicker bottom 33 to urge the tip further towards the obstruction. The elongated shape of scoops 31 and 32 shields a length of the obstruction that can be treated without requiring to re-position the scoop in the vessel.

While the present invention has been illustrated with specific embodiments, it should be understood that modifications and substitutions may be made within the spirit of the invention and the scope of the claims. For example, to enhance the flexibility of the rotary catheter, the spiraled wire 17 can be lengthened and the flexible hollow shaft portion 16 shortened or vice versa. In such a case of using a long shaft portion 16, an additional portion of a spiraled wire may optionally be attached to the proximal end of the flexible hollow shaft portion 16. Such a configuration may be useful in a long rotary catheter needed to reach the heart or brain while entering the vasculature at the groin region. In such an application, the additional proximal spiraled wire portion provides enhanced flexibility at the entry region, whereas, the distal spiraled wire portion 17 provides enhanced flexibility needed in the tortuous coronary vasculature, while the lengthened flexible hollow shaft portion 16 is sufficiently flexible to be disposed in the relatively intermediate vasculature (e.g., iliac, aorta). Such staggered construction reduces the system's bulk and the longitudinal flexibility of the flexible hollow shaft 14.

The sides 22 and 24 can be made slightly curved or tilted, from the parallel position depicted in FIG. 3, to form a dihedral angle (please note FIG. 16), so as to increase the passages 22' and 24' while narrowing the crown, or conversely, they be made so as to increase the crown to provide a larger bearing area for the tip as it slides over a wall of the vessel 13.

Figure 14:
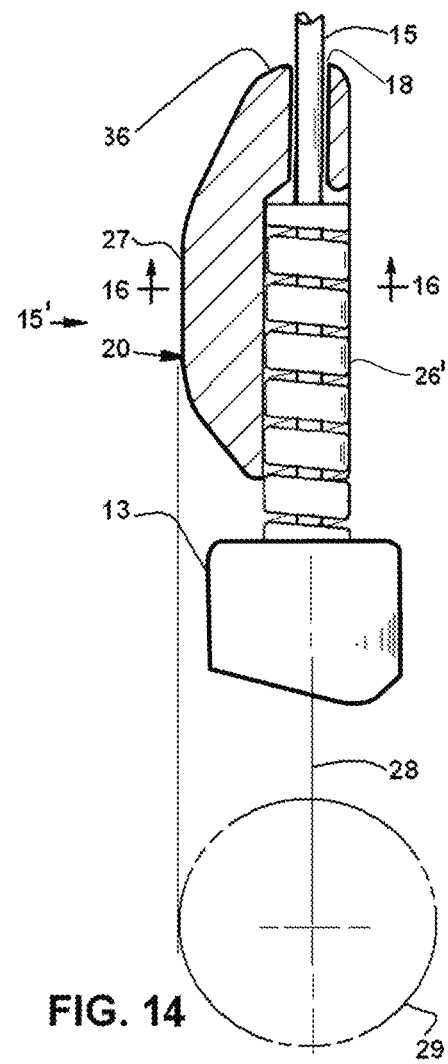
FIG. 14 shows another modification of the rotary catheter, wherein a distal end section of the spiraled wire that is extended out of the distal end of the flexible tube is straightened by a guidewire that is disposed through it.

The guidewire enables delivering the rotary catheter through tortuous vasculature to remote occlusions and operating it with an enhanced degree of safety. However, a rotary catheter, according to the present invention, is adaptable to occasionally operate with the guidewire withdrawn proximally into the flexible hollow shaft to address specific clinical scenarios. One such scenario is adapting the rotary catheter to cross total occlusion as was previously discussed. Another scenario relates to treating large vessels (e.g., blood vessels in the pelvic area, hemodialysis fistula, aneurysm) with the rotary catheter shown in FIGS. 14-18. FIG. 14 shows a distal end section of the spiraled wire 17 that extends out of the distal end of the flexible tube 13 being straightened by a guidewire 15 that is disposed through it.

However, the distal end section of the spiraled wire is pre-formed to automatically assume a curved shape when the guidewire 15 is withdrawn from it (please note FIG. 17) and to thereby increase the offset of the tip 20. This in turn substantially increases the area within circle 29' that the tip sweeps (please note FIG. 17), as compared to the area within circle 29 (please note FIGS. 14 and 3). It should however be understood that the actual cross section of the tunnel that is opened by the tip will also be affected by, for example, the topography and material of the surrounding vessel and obstruction and the rotational speed of the flexible hollow shaft and tip. Thus, when a larger segment of a vessel has to be treated, the guidewire can be withdrawn proximally out of the spiraled wire, allowing the pre-formed distal end section of the spiraled wire to automatically assume its pre-formed curved shape shown in FIG. 17 and thereby increase the tip's sweep. Optionally, the user can gradually withdraw the guidewire to achieve a corresponding gradual curving of the distal end section of the spiraled wire and conversely, in the absence of the guidewire, the user can reduce the curvature by advancing the flexible tube as shown in FIG. 1a. After opening the large vessel, the guidewire can be re-advanced distally through the tip to reassume the configuration shown in FIG. 14 and the guidewire may be left in the vessel after withdrawing the rotary catheter to facilitate for follow-up procedure (e.g., angioplasty and/or deployment of a stent).

Figure 16:
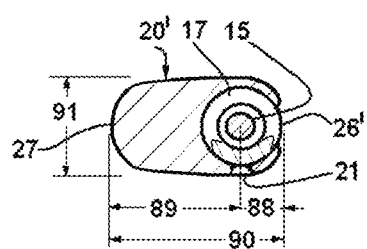
FIG. 16 is cross sectional view of the tip, along a plane 16-16 marked on FIG. 14, which shows a further modification of the tip.

FIG. 16 is cross sectional view of a modified tip 20', along a plane 16-16 marked on FIG. 14. The tip has slightly curved sides and an enhanced effective radius 89 which is achieved by reducing the offset 88 and essentially using the spiraled wire as a base 26'. The modification of the tip effectively minimizes the offset of the base and enhances an offset of the crown.

Figure 15:
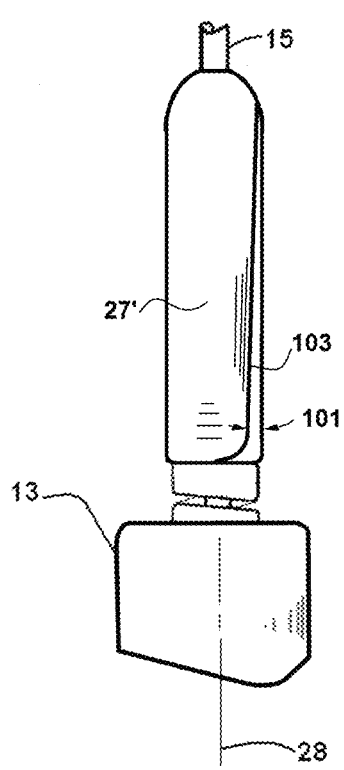
FIG. 15 shows the rotary catheter as viewed in the direction of arrow 15' marked on FIG. 14, wherein the first side of the tip is inclined.

FIG. 15 shows a further modification of the tip (viewed in the direction of arrow 15' marked on FIG. 14) where a first side of the tip 103 is inclined by an angle 101 so that it propels fluid and particles of the obstruction proximally when the tip rotates in a first direction.

Figure 18:
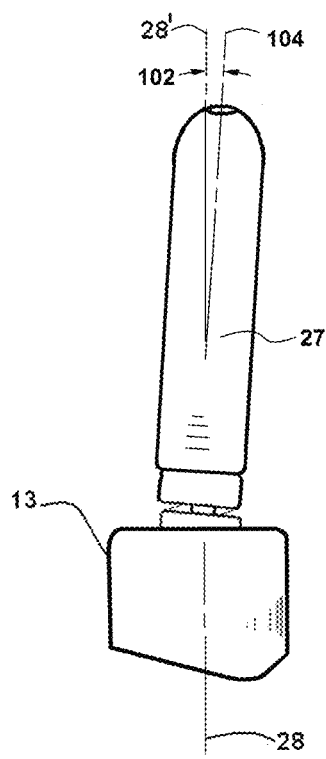
FIG. 18 shows the rotary catheter viewed in the direction of arrow 18' marked on FIG. 17.
Figure 17:
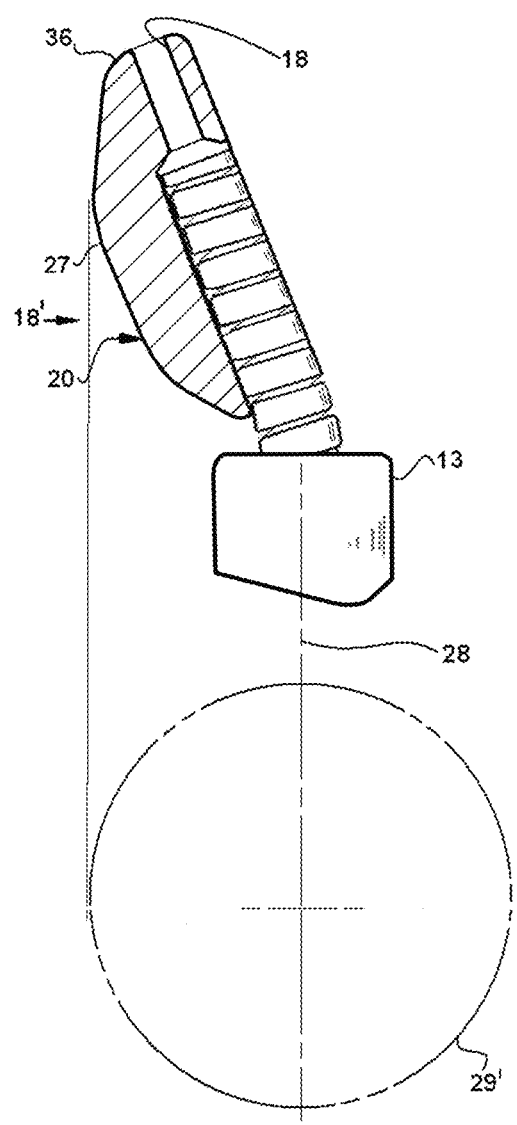
FIG. 17 shows the modified rotary catheter of FIG. 14 wherein the distal end section of the spiraled wire automatically assumed a curved shape and increased the offset of the tip in the absence of the guidewire.

FIG. 18 shows a further modification of the flexible hollow shaft (viewed in the direction of arrow 18' marked on FIG. 17) wherein, in the absence of a guidewire, it also tilts by an angle 102 so that it propels fluid and particles of the obstruction proximally when it rotates in a first direction. The line 28' is a continuation of line 28, whereas line 104 is a longitudinal axis of the spiraled wire section that is in the tilted tip. In FIG. 18, a distal end section of the flexible hollow shaft is extended out of the distal end of the flexible tube and is pre-formed to automatically incline the tip, in response to the guidewire being withdrawn from within the distal end section of the hollow shaft.

A seal-set for the preferred embodiment can be manufactured by affixing a bearing defining a first bore to a seal material, inserting a drill slightly smaller than a diameter of the bore so that the bore rotatably and accurately supports the drill, rotating and advancing the drill to cut a second bore in the seal material that is slightly smaller and concentric relative to the first bore. In various embodiments, the drill can be a hollow shaft with a sharp tip, a single point cutter or a hypodermic needle. Preferably, the seal material is an elastomer, such as, for example, silicone. Also, the seal material is a rotary seal material.

Another embodiment of the rotary catheter drive unit contains a motor and a seal-set, a second bore of the motor being power transmittingly connected to a flexible shaft that is rotatably disposed through the seal-set, the seal-set comprising a bearing and an adjacent seal defining a first and a second concentric bores, respectively, the first bore being slightly larger than the diameter of the shaft so that it rotatably and accurately supports the shaft, the second bore being slightly smaller than the diameter so that it seals around the shaft, the bearing aligning the shaft, so that it is concentric with the second bore, by deflecting the shaft to compensate for eccentricity and misalignment of the second bore relative to the second bore of the motor. The rotary catheter drive unit cam also contain one seal-set distally relative to the motor and a second seal-set proximally relative to the motor, wherein the flexible shaft passes through both the seal-sets and the motor. The shaft can be hollow, extends out of the proximal end of the housing and is slideable and rotatable over a guidewire. A slideable proximal extension of the housing contain a seal adapted to cross and exposes an open distal end of the hollow shaft when the proximal extension is slid distally and, vice versa. The seal can be adapted to cross the distal end of the hollow shaft when the proximal extension is slid proximally and close.

The invention has been described in detail with particular reference to certain preferred embodiments thereof, but it will be understood that variations and modifications can be included within the spirit and scope of the invention.

The invention claimed is:

1. A motor drive for a rotary medical device comprising:
   at least one seal-set which comprises
   a bearing defining a bearing bore,
   a seal defining a seal bore, said seal mounted adjacent to said bearing with said seal bore being concentric with said bearing bore,
   in combination with
   a motor having an output shaft,
   a flexible shaft, having a diameter smaller than said bearing bore and larger than said seal bore, being concentrically connected to said output shaft, said flexible shaft passing through and being deflected by said bearing bore to be aligned with and to interferencingly fit through said seal bore and hydraulically seal said seal bore.

2. The motor drive according to claim 1 wherein said motor output shaft is hollow and said flexible shaft is nested in and connected to said output shaft.

3. The motor drive according to claim 1 where said seal comprises a layer of elastomeric material defining a bore.

4. The motor drive according to claim 1 where said seal is made of an elastomeric material that has a toroid shape.

5. The motor drive according to claim 1 where said seal is made of an elastomeric material that has a torus shape.

6. A motor drive for a rotary medical device having two seal-set which comprises in combination:
   a motor having a hollow output shaft,
   a flexible shaft concentrically connected to said output shaft, wherein said flexible shaft is hollow and has a proximal end and a distal end that extend proximally and distally, respectively, from said output shaft,
   a proximal seal, defining a bore that is smaller than a diameter of said proximal end of said flexible shaft, being mounted adjacent to a proximal bearing which also defines a bore that is larger than said diameter of said flexible shaft, wherein said bores are concentric, said proximal end of said flexible shaft passing through said proximal bearing bore which sufficiently deflects it to be aligned with said proximal seal bore and to interferencingly fit through and hydraulically seal said proximal seal bore, and,
   a distal seal, defining a bore that is smaller than a diameter of said distal end of said flexible shaft, being mounted adjacent to a distal bearing which also defines a bore that is larger than said diameter of said flexible shaft, wherein said bores are concentric, said distal end of said flexible shaft passing through said distal bearing bore which deflects it to be aligned with said distal seal bore and interferencingly fit through and hydraulically seal said distal seal bore.

* * * * *